United States Patent [19]

Gagliardi

[11] 4,061,675
[45] Dec. 6, 1977

[54] PROCESS FOR THE SYNTHESIS OF UREA FROM CARBON DIOXIDE AND AMMONIA

[75] Inventor: Renzo Gagliardi, Terni, Italy

[73] Assignee: Snam Progetti S.p.A., Milan, Italy

[21] Appl. No.: 710,323

[22] Filed: July 30, 1976

[30] Foreign Application Priority Data

Oct. 15, 1969  Italy .................................. 40806/69

[51] Int. Cl.$^2$ ........................................... C07C 126/02
[52] U.S. Cl. .............................................. 260/555 A
[58] Field of Search ................................. 260/555 A; 423/359–363

[56] References Cited

U.S. PATENT DOCUMENTS

| 3,046,307 | 7/1962 | Bochinski ...................... 260/555 A |
| 3,069,234 | 12/1962 | Cook et al. .................. 260/555 A X |
| 3,674,847 | 7/1972 | Kaasenbrood et al. ......... 260/555 A |

OTHER PUBLICATIONS

Powell, "Urea Process Technology," (1968) pp. 136–138.

Primary Examiner—Edward J. Meros
Attorney, Agent, or Firm—Young & Thompson

[57] ABSTRACT

Urea is produced from ammonia synthesis effluent containing hydrogen, nitrogen, methane and argon, which is reacted with carbon dioxide to form ammonium carbamate. The hot ammonia synthesis effluent is contacted with the liquid effluents from the area synthesis reactor to dissociate the carbamate contained in said effluents into a gaseous effluent containing ammonia, carbon dioxide and oxygen, and to produce a further liquid reaction product containing urea. Oxygen is removed from the carbamate dissociation effluent, which is then fed to the ammonia synthesis step.

3 Claims, 1 Drawing Figure

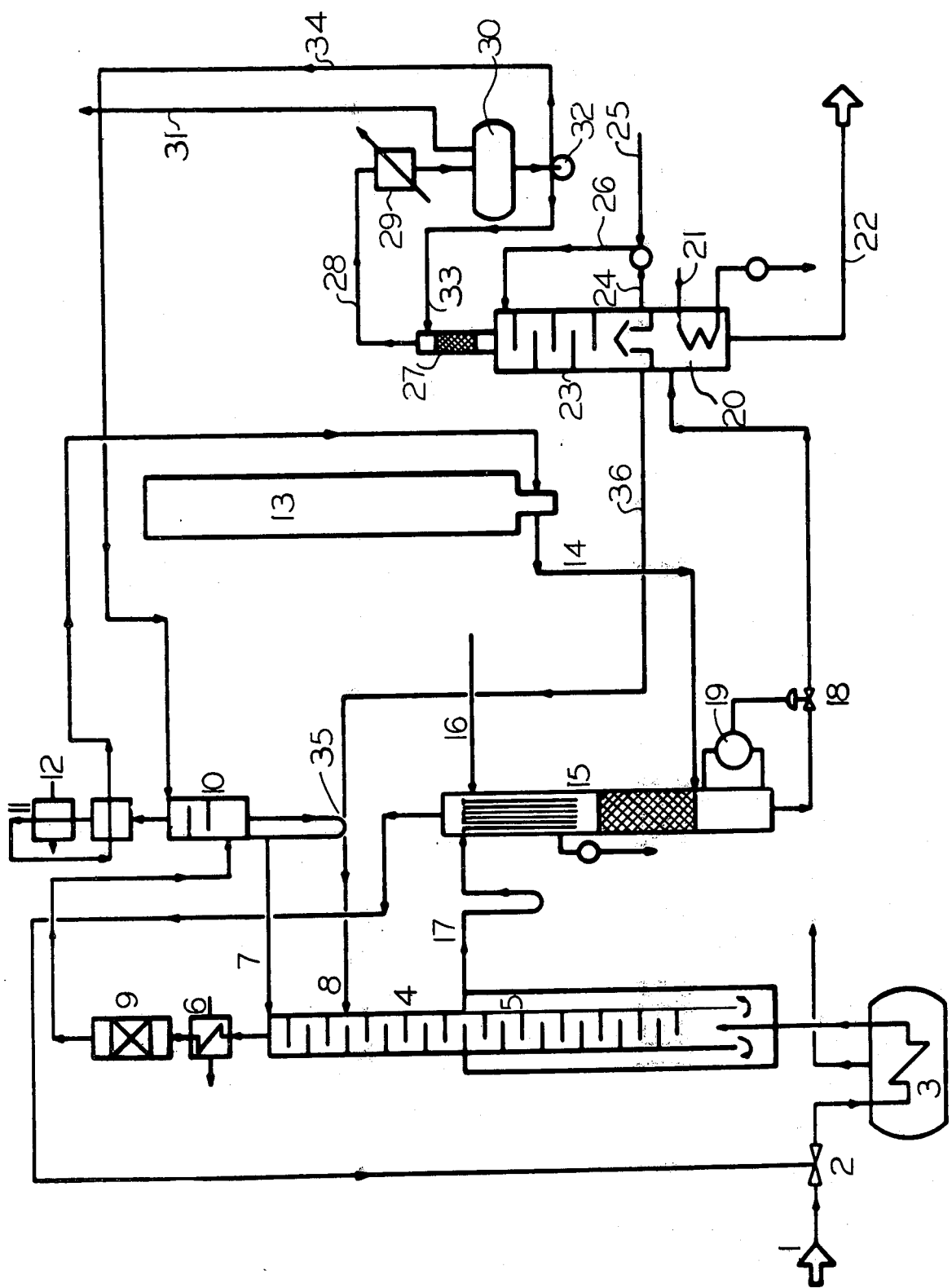

PROCESS FOR THE SYNTHESIS OF UREA FROM CARBON DIOXIDE AND AMMONIA

This application is a continuation-in-part of my abandoned application Ser. No. 79,608, filed Oct. 9, 1970, entitled "Process for the Synthesis of Urea from Carbon Dioxide and Ammonia".

The present invention relates to a new process for the production of urea starting from gaseous ammonia and carbon dioxide in the presence of other gases such as $H_2$, $N_2$, $CH_4$, and Argon. It is known that the procedures presently used in industry consist in reacting together ammonia and carbon dioxide substantially pure or in the presence of a limited amount of water, in a container where temperature and pressure are maintained at such a level as to allow the ammonium carbamate, formed from the reaction of $NH_3$ and $CO_2$, to partly transform itself into urea and water, according to an equilibrium reaction.

In order to produce pure urea it is necessary, therefore, to separate the ammonium carbamate from the urea and water solution and to recycle it into the synthesis reactor together with the $NH_3$ and the $CO_2$ fed in.

Description of old processes no longer used is omitted; some perform the ammonium carbamate recycling by expanding the urea-carbamate mixture to a pressure considerably lower than that of synthesis and at the same time, heat is supplied in order to obtain the dissociation of the ammonium carbamate to gaseous $CO_2$ and $NH_3$.

Normally these components are absorbed with water and the obtained solution is recycled to the synthesis reactor. It is also known that it is attempted as much as possible to limit the amount of recycling $H_2O$ to avoid the decrease in yield of the transformation of ammonium carbamate into urea in the synthesis reactor. Some recent industrial processes have succeeded in limiting greatly the recycling of carbamate solutions, because the dissociation of the carbamate has been performed at the synthesis pressure itself.

The greater part of the $CO_2$ and the $NH_3$ resulting from the carbamate dissociation, can thus go back to the reaction zone, in a gaseous form without the use of compressors.

In this type of plant the dissociation is generally performed in special heat exchangers, inside of which, in contact with the urea-carbamate-water-$NH_3$ mixture coming from the reactor, the main stream of the $CO_2$ (or of the $NH_3$) is fed through.

The $CO_2$ (or the $NH_3$) added to the gaseous phase promotes the dissociation, because it shifts the equilibrium.

The heat is supplied by steam at a temperature generally not lower than 200° C.

The ammonia and carbon dioxide fed in come separately from one or more ammonia plants. Generally the $NH_3$ is available in a liquid and anhydrous state and the $CO_2$ is a gaseous state and at a pressure slightly higher than atmospheric.

A modern process for the production of $NH_3$ consists essentially of the following operations: oxidation of a hydrocarbon to obtain a gas with a high hydrogen and nitrogen content necessary for ammonia synthesis. The oxidation may be performed at the same time and/or separately by means of steam, oxygen, or air.

The gas for the ammonia synthesis thus obtained together with the hydrogen and nitrogen and with a small amount of methane and argon, contains carbon dioxide and carbon monoxide, which are substances that cannot be tolerated by the catalysts used for the synthesis of ammonia from nitrogen and hydrogen.

Therefore appropriate operations are carried out to remove the $CO_2$ and the CO completely from the gases which come in contact with the catalyst for ammonia synthesis.

It is known, moreover, that the ammonia formed in a synthesis reactor, comes out in gaseous state together with a certain amount of unreacted gases. Besides, since the formation of ammonia is an exothermic reaction, the gases from the synthesis reactor are at a higher temperature than at entry.

Therefore the effluents of the reactor for ammonia synthesis must be cooled to a considerably lower temperature level, to allow the recovery of ammonia by condensation, before the unreacted gases are recycled to the synthesis gas together with the $H_2$ and $N_2$ fed in.

Generally the heat available is at a temperature level so low that it is not convenient for production of steam and, besides, if the circuit pressures are not so high as to allow the use of water as cooling fluid, the heat must be removed by a refrigerating circuit and therefore with a further energy expense.

A urea synthesis process according to the present invention will now be described. In this process, the condensation of the ammonia produced by the synthesis reactor is not necessary, and the separation of the carbon dioxide from the hydrogen and the nitrogen intended for the ammonia synthesis, occurs after the compression of the gases to the $NH_3$ synthesis pressure.

In this process the heat developed by the ammonia synthesis is completely utilized for the ammonia carbamate dissociation.

This utilization is performed by mixing the gaseous effluents proceeding, without cooling, from the ammonia synthesis, with the liquid effluents proceeding from the urea synthesis and containing the carbamate not transformed into urea. In this way, there exist physical-chemical conditions owing to which part of the carbamate is dissociated into $NH_3$ and $CO_2$. The heat necessary to decompose the carbamate is therefore supplied by the heat available in the gases from the $NH_3$ synthesis and, whenever it is not sufficient, it can be augmented by utilizing steam at a suitable pressure and temperature, by means of heat exchange surfaces.

The process therefore, besides allowing a considerable saving in steam as compared to other processes, can considerably reduce the complications connected with the recycling of the carbamate not transformed into urea and allows the urea-water solution, expanded to pressures lower than that of synthesis, to contain a limited amount of free ammonia since the said solution undergoes a distillation in a stream of superheated inerts.

The carbamate-urea system synthesis acts also as a scrubber of the gas for the $NH_3$ synthesis.

While the carbon monoxide has been eliminated catalytically before the compression to a high pressure, the $CO_2$ is completely eliminated by washing with the carbamate-$NH_3$-water solution recycled from the low pressure system and, finally with liquid $NH_3$.

Since the gases fed in for the $NH_3$ synthesis may contain traces of $O_2$ coming from the catalytic oxidation of CO, a de-oxo reactor is set up upstream of the $NH_3$ system. It is preferred to install the de-oxo reactor upstream the $NH_3$ synthesis and downstream of the urea reactor, since the existing $O_2$ present constitutes a corrosion inhibitor in the urea synthesis reactor.

An example of application of the described process, in any case not limitative, is illustrated in the attached drawing.

In the said drawing the ammonia synthesis gas 1, CO-free but containing all the original carbon oxidized to $CO_2$, is mixed in the ejector 2 (or in a circulating equipment) with the recycle gas proceeding from the tower 15.

The $CO_2$ and the $NH_3$ present in the gaseous state, together with the $N_2$, $H_2$ and $CH_4$ combine to a large extent, at a convenient pressure and temperature, to form ammonium carbamate, while the heat of reaction is eliminated by means of the boiler-condenser 3.

The carbamate mixture formed, together with the uncondensed gas is sent to the bottom of the plate-tower 4. Because of the carbamate-$NH_3$-water solution falling from the head of the said tower, practically all the free $CO_2$ combines with the $NH_3$ present. The water-carbamate liquid goes up to the zone 5 where it stays to transform itself partly unto urea according to the known equilibrium reaction. Through the syphon 17 the reaction mixture is conveyed into the tower 15. In tower 15, which can be provided either with plates or with filling bodies, an intimate contact occurs between the effluent 14 from the ammonia synthesis reactor 13 and the transformation products of the carbamate proceeding from the reactor zone 5.

The heat contained in the products 14, which are at a temperature of 100° to 600° C., is ceded completely during the contact until the temperature of the product in tower 15 is reached. The remaining heat necessary for the carbamate dissociation is supplied in the head of the tower 15, through a heat exchanger, heated with the steam 16.

Because of the changes in equilibrium conditions of the carbamate in tower 15 which operates under a pressure of 100 to 1000 atmospheres, most of it is subjected to a dissociation into $NH_3$ and $CO_2$ and these gases flow from the head of the tower 15 to be recycled into tower 4 through the ejector 2.

From the bottom of the tower 15 the solution urea-water-non-transformed carbamate is drawn and expanded to lower pressures through valve 18 under control of a liquid level control device 19. The lower pressure liquid then passes to the lower end of the distillation column 20 provided with a reboiler 21 for removing the more volatile constituents thereof. The liquid bottoms, which is an aqeuous solution of urea, is removed at 22 as product.

Vapors rising in column 20 are subjected to rectification in an upper portion 23 thereof. A liquid fraction from the lower end of the rectification section is withdrawn at 24 and is an aqueous solution of ammonium carbamate and ammonium carbonate. It is admixed with water introduced at 25 and proceeds through conduit 26 to the upper end of rectification section 23, where it serves as reflux. The gaseous overhead from rectification section 23 passes through a washing column 27 where the last traces of carbon dioxide not yet absorbed are removed in a stream of liquid ammonia. The vapor from column 27, which is ammonia and inert gases, passes through conduit 28 to a water-cooled condenser 29 from which liquid ammonia is condensed and stored in container 30. The inert gases leave the system and are vented through a purge conduit 31.

Liquid ammonia from container 30 is pumped in two directions by a pump 32, a stream 33 proceeding to column 27 for carbon dioxide washing purposes, and another stream 34 proceeding to washing column 10. Liquid ammonia from the bottom of column 10 is divided at 35 and a portion joins ammonium carbamate and ammonium carbonate solution in conduit 36 and is introduced into tower 4 at 8; while further liquid ammonia is introduced at 7 to the top of tower 4 for reflux purposes.

Thus the incondensibles rising in tower 4 encounter sequentially the carbamate-water-ammonia solution introduced at 8, and then the stream of liquid ammonia introduced at 7. The overhead from tower 4 passes through a water-cooled condenser 6, which provides additional liquid ammonia reflux and thus eliminates all $CO_2$.

However, there will in the stream emerging from condenser 6, be a small amount of oxygen. Therefore, a de-ozo reactor 9 is provided, which eliminates this oxygen by transforming it to $H_2O$.

The stream of vapor, thus freed from oxygen, then proceeds to column 10 which has a condenser 11 cooled by refrigerating fluid 12, for condensing any traces of $H_2O$, whereby the thus dried ammonia synthesis gas can proceed to the synthesis reactor 13, which operates under a pressure of 100 to 1000 atmospheres.

Having thus described the present invention, what is claimed is:

1. In a method of making urea, which comprises synthesizing ammonia by reacting a gaseous mixture containing nitrogen and hydrogen to give a gaseous ammonia synthesis product which also contains hydrogen, nitrogen, methane and argon, reacting the ammonia synthesis product with carbon dioxide to form a liquid reaction product containing ammonium carbamate, and dissociating said ammonium carbamate to form urea; the improvement comprising contacting the hot ammonia synthesis effluent with the liquid effluent from the urea synthesis reactor in order to dissociate the ammonium carbamate contained in said effluents into a gaseous effluent containing ammonia, carbon dioxide and oxygen and to produce a further liquid product containing urea, removing oxygen from said carbamate dissociation effluent, and thereafter feeding the deoxygenated effluent to the ammonia synthesis step.

2. A method according to claim 1, in which the temperature of the ammonia synthesis effluent is in the range from 100° to 600° C.

3. A method according to claim 2, in which both the ammonia synthesis and the formation of the further liquid product are carried out at a pressure of 100 to 1000 atmospheres.

* * * * *